(12) United States Patent
Yu et al.

(10) Patent No.: US 10,335,492 B2
(45) Date of Patent: Jul. 2, 2019

(54) INCREASING SERUM HALF-LIFE OF HUMAN IL-11 VARIANTS BY N-TERMINAL BRANCHED PEGYLATION

(71) Applicant: Nansha Biologics (Hong Kong) Limited, Central (HK)

(72) Inventors: Kuo-Ming Yu, Taipei (TW); Qui-Lim Choo, El Cerrito, CA (US); Manson Fok, Hong Kong (CN); Johnson Yiu-Nam Lau, Houston, TX (US)

(73) Assignee: NANSHA BIOLOGICS (HONG KONG) LIMITED, Hong Kong (HK)

( * ) Notice: Subject to any disclaimer, the term of this patent is extended or adjusted under 35 U.S.C. 154(b) by 0 days.

(21) Appl. No.: 15/554,415

(22) PCT Filed: Mar. 1, 2016

(86) PCT No.: PCT/US2016/020294
§ 371 (c)(1),
(2) Date: Aug. 29, 2017

(87) PCT Pub. No.: WO2016/140983
PCT Pub. Date: Sep. 9, 2016

(65) Prior Publication Data
US 2018/0036418 A1   Feb. 8, 2018

Related U.S. Application Data

(60) Provisional application No. 62/127,748, filed on Mar. 3, 2015.

(51) Int. Cl.
| | |
|---|---|
| *A61K 47/60* | (2017.01) |
| *A61K 38/00* | (2006.01) |
| *A61K 38/20* | (2006.01) |
| *C07K 14/54* | (2006.01) |
| *A61K 9/00* | (2006.01) |
| *A61K 45/00* | (2006.01) |

(52) U.S. Cl.
CPC ............ *A61K 47/60* (2017.08); *A61K 9/0019* (2013.01); *A61K 38/2073* (2013.01); *A61K 45/00* (2013.01); *C07K 14/5431* (2013.01); *A61K 38/00* (2013.01)

(58) Field of Classification Search
None
See application file for complete search history.

(56) References Cited

U.S. PATENT DOCUMENTS

| | | |
|---|---|---|
| 8,133,480 B2 | 3/2012 | Cox, III |
| 8,716,446 B2 | 5/2014 | Jung et al. |
| 2016/0000901 A1 | 1/2016 | Blackburn et al. |

FOREIGN PATENT DOCUMENTS

| | | | | |
|---|---|---|---|---|
| JP | 2005281302 A | | 10/2005 | |
| WO | WO2010024557 | * | 4/2010 | ............ A61K 38/20 |
| WO | 2013020079 A2 | | 2/2013 | |
| WO | 2014008242 A1 | | 1/2014 | |

OTHER PUBLICATIONS

Sequence listing from the priority document of the reference—Application # WO2012US49582 Aug. 3, 2012 (Year: 2012).*
Julia Karow, "Mediation of interleukin-11-dependent biological responses by a soluble form of the interleukin-11 receptor" Biochemical Journal, vol. 318: pp. 489-49; Sep 1, 1996.
Application No. PCT/US2016/020356 (Avalon Biologics Limited et al.) Application date: Mar. 2, 2016.
International Search Report for PCT/US2016/20294 filed Mar. 1, 2016, ISR dated Jun. 1, 2016.
Takagi, Akira et al., "Enhanced pharmacological activity of recombinant human interleukin-11 (rhIL11) by chemical modification with polyethylene glycol" Journal of Controlled Release; vol. 119, Issue 3, Jun. 22, 2007, pp. 271-278.
Yanaka et al., "Non-core region modulates interleukin-I I signaling activity: generation of agonist and antagonist variants." Journal . Biol. Chem., 286:8085-8093.

* cited by examiner

*Primary Examiner* — Elly-Gerald Stoica
(74) *Attorney, Agent, or Firm* — Fish IP Law, LLP

(57) ABSTRACT

Compositions and methods are presented in which recombinant IL-11 is PEGylated to achieve improved half-life in serum while having desirable therapeutic activity and presenting less side-effects. Most preferably, the IL-11 is an N-terminally truncated human or humanized IL-11 and has a 20 Kd or 40 Kd branched PEG moiety, Y- or comb-shaped in particular, coupled to the N-terminal amino group. Such compounds are characterized by substantially increased stability in serum and sustained biological activity while exhibiting significantly reduced plasma expansion.

7 Claims, 10 Drawing Sheets
Specification includes a Sequence Listing.

|   |   |   |   |   |   |
|---|---|---|---|---|---|
| 10 | 20 | 30 | 40 | 50 | 60 |
| GPPPGPPRVS | PDPRAELDST | VLLTRSLLAD | TRQLAAQLRD | KFPADGDHNL | DSLPTLAMSA |

Helix A

|   |   |   |   |   |   |
|---|---|---|---|---|---|
| 70 | 80 | 90 | 100 | 110 | 120 |
| GALGALQLPG | VLTRLRADLL | SYLRHVQWLR | RAGGSSLKTL | EPELGTLQAR | LDRLLRRLQL |

Helix B                               Helix C

|   |   |   |   |   |
|---|---|---|---|---|
| 130 | 140 | 150 | 160 | 170 |
| LMSRLALPQP | PPDPPAPPLA | PPSSAWGGIR | AAHAILGGLH | LTLDWAVRGL     LLLKTRL |

Helix D

|                                      | IL-11  | I20NY  | I20NY2 | I20NL  |
|--------------------------------------|--------|--------|--------|--------|
| EC50(pM)                             | 30.49  | 191.60 | 1012.0 | 239.80 |
| R square                             | 0.9918 | 0.9979 | 0.9988 | 0.9954 |
| Potency ratio to unmodified IL-11    | 1      | 0.16   | 0.03   | 0.13   |

|                                      | IL-11  | I40NY  | I40KY  | I40NX  |
|--------------------------------------|--------|--------|--------|--------|
| EC50(pM)                             | 30.80  | 277.20 | 536.40 | 292.90 |
| R square                             | 0.9957 | 0.9926 | 0.9991 | 0.9968 |
| Potency ratio to unmodified IL-11    | 1      | 0.11   | 0.06   | 0.11   |

SEQUENCE LISTING

```
<160> NUMBER OF SEQ ID NOS: 1

<210> SEQ ID NO 1
<211> LENGTH: 177
<212> TYPE: PRT
<213> ORGANISM: Homo sapiens
<220> FEATURE:
<221> NAME/KEY: PEPTIDE
<222> LOCATION: (1)..(177)
<223> OTHER INFORMATION: human IL-11 lacking N-terminal P

<400> SEQUENCE: 1

Gly Pro Pro Pro Gly Pro Pro Arg Val Ser Pro Asp Pro Arg Ala Glu
1               5                   10                  15

Leu Asp Ser Thr Val Leu Leu Thr Arg Ser Leu Leu Ala Asp Thr Arg
                20                  25                  30

Gln Leu Ala Ala Gln Leu Arg Asp Lys Phe Pro Ala Asp Gly Asp His
            35                  40                  45

Asn Leu Asp Ser Leu Pro Thr Leu Ala Met Ser Ala Gly Ala Leu Gly
        50                  55                  60

Ala Leu Gln Leu Pro Gly Val Leu Thr Arg Leu Arg Ala Asp Leu Leu
65                  70                  75                  80

Ser Tyr Leu Arg His Val Gln Trp Leu Arg Arg Ala Gly Gly Ser Ser
                85                  90                  95

Leu Lys Thr Leu Glu Pro Glu Leu Gly Thr Leu Gln Ala Arg Leu Asp
                100                 105                 110

Arg Leu Leu Arg Arg Leu Gln Leu Leu Met Ser Arg Leu Ala Leu Pro
            115                 120                 125

Gln Pro Pro Pro Asp Pro Pro Ala Pro Pro Leu Ala Pro Pro Ser Ser
        130                 135                 140

Ala Trp Gly Gly Ile Arg Ala Ala His Ala Ile Leu Gly Gly Leu His
145                 150                 155                 160

Leu Thr Leu Asp Trp Ala Val Arg Gly Leu Leu Leu Leu Lys Thr Arg
                165                 170                 175

Leu
```

INCREASING SERUM HALF-LIFE OF HUMAN IL-11 VARIANTS BY N-TERMINAL BRANCHED PEGYLATION

This application claims priority to our copending U.S. provisional application with the Ser. No. 62/127,748, which was filed 3 Mar. 15, and which is incorporated by reference herein.

FIELD OF THE INVENTION

The field of the invention is pharmaceutical compositions and methods, especially as they relate to PEGylated Interleukin 11 (IL-11).

BACKGROUND OF THE INVENTION

The background description includes information that may be useful in understanding the present invention. It is not an admission that any of the information provided herein is prior art or relevant to the presently claimed invention, or that any publication specifically or implicitly referenced is prior art. All publications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Chemotherapy-induced thrombocytopenia remains an unmet medical need because the current treating regimen employs transfusion of platelets that may be in short supply and carry a risk of viral contamination. On the other hand, recombinant human IL-11 can be given to a patient to stimulate platelet production. However IL-11 administration requires daily dosing, leading to marginal clinical efficacy and plasma expansion.

IL-11 is a cytokine and acts as a major signaling agent in hematopoiesis, and especially in the stimulation of megakaryocyte maturation. Action of IL-11 is typically mediated by the IL-11 receptor and glycoprotein gp130 with subsequent phosphorylation/activation of gp130. Clinical uses for IL-11 include treatment of side effects associated with chemotherapy, which is thought to enhance megakaryocytopoiesis and increase platelet counts. Recombinant human IL-11 is commercially available as NEUMEGA® (Oprelvekin, Wyeth-Ayerst) and is approved for the prevention of severe thrombocytopenia and the reduction of the need for platelet transfusions following myelosuppressive chemotherapy in adult patients with non-myeloid malignancies who are at high risk of severe thrombocytopenia. NEUMEGA® is typically supplied in a single use vial containing 5 mg IL-11 as a lyophilized powder for reconstitution with 1 mL sterile water for injection (administered at a dose of 25-50 µg/kg/day). The most frequent adverse event associated with NEUMEGA™ is plasma expansion leading to life-threatening atrial arrhythmias, syncope, dyspnea, congestive heart failure, and pulmonary edema.

IL-11 is cleared from the circulatory system relatively quickly and as such requires multiple injections. For example, Neumega™ subcutaneously administered in healthy men has a terminal half-life about 6.9 hours (Product Insert of Neumega™). The poor pharmacokinetics such as rapid renal excretion and proteolytic digestion, as well as its associated adverse effect often reduce clinical prevalence. Moreover, daily injection also means hospitalization to manage adverse event that not only adds on medical expense but also damages quality of life to patients. As a result, platelet transfusion remains the gold-standard for treating chemotherapy-induced thrombocytopenia (CIT).

Several attempts have been undertaken in the art to increase serum stability while maintaining beneficial therapeutic potential of such compositions. For example, US 2010/0098658 reports an IL-11 analog (mIL-11) in association with a polymer (PEG) that exhibited enhanced resistance to acidolysis and increased serum half-life. In another attempt to stabilize IL-11, as described in U.S. Pat. No. 8,133,480, cysteine variants of IL-11 were prepared and selected muteins were further modified with PEG to increase serum stability. While these modifications have improved serum stability or half-life of IL-11 to at least some degree, one or more disadvantages nevertheless remain, including marginal efficacy in myelosuppressive animals, complexity in production, repeated dosing, and formulation into injectable solution.

Because of lacking cysteine residues in IL-11, the '480 patent describes insertion of a cysteine residue in the C-terminal amino acid sequence, conferring a functional group to allow conjugation of a thiol-reactive polyethylene glycol chain. Although the biological activity was conserved, the introduction of cysteine may yield intermolecular dimers and the production yield of insect cells may be lower than bacterial production. Additionally the serum half-life of so modified IL-11 when administered intravenously in male Sprague-Dawley rats was about 5.6 hr for 40 KD PEGylation, which is less than desirable. Moreover, in animal studies using cyclophosphamide-treated rats, the efficacy was marginal with the-other-day dosing scheme. Another employed PEG conjugation onto N-terminally truncated sequence of IL-11 with 20 KD PEG via amine or amide bonding was described in US 2010/0098658. Although the N-terminal truncation did not reduce its biological activity, the serum half-life administered subcutaneously in male Sprague-Dawley rats was about 8.5 hr, again falling short of desirable stability. Additionally, the efficacy in an animal disease model was unknown.

Linear or branched PEG of 20 KD conjugating onto amine groups of IL-11 was reported (Takagi et al. 2007, "Enhanced pharmacological activity of recombinant human interleukin-11 (rhIL11) by chemical modification with polyethylene glycol." *J Control Release*, 119(3):271-278), such unspecific conjugation often resulted in multiple PEGylation via reaction with lysine, histidine, and tyrosine residues as well as N-terminal amines.

Other reports have demonstrated certain carbohydrate modifications on the "non-core" regions of IL-11 such as N-terminus and loops enhanced cell-stimulatory activities, suggesting these regions are perhaps designed to limit biological activity of IL-11 (Yanaka et al. 2011, "Non-core region modulates interleukin-11 signaling activity: generation of agonist and antagonist variants." *J. Biol. Chem.*, 286:8085-8093). However, no desirable modification was reported with stabilities and activities above unmodified IL-11.

Thus, even though several methods of stabilizing IL-11 are known in the art, all or almost all have one or more drawbacks, such as limited efficacy and requirement for repeated dosing. More importantly, even in modified form, adverse effects of IL-11 (e.g., plasma expansion) were not reduced. Therefore, there remains a need for improved compositions and methods to stabilize IL-11 while simultaneously alleviate adverse effects.

SUMMARY OF THE INVENTION

The inventive subject matter is directed to compounds, compositions, and methods for improving stability and half-life time of IL-11 in serum while maintaining biological activity and mitigating side-effects. In especially preferred aspects, the inventors have discovered that the amino acid position, manner of attachment, and type of PEG is critical to producing stable and biologically active PEGylated IL-11, and particularly preferred PEGylated IL-11 will have the same sequence as native human IL-11 but lack the N-terminal first amino acid, proline. Moreover, such IL-11 will preferably be covalently modified at the N-terminus with a possible secondary site at certain lysine residues within the polypeptide chain. Most typically, the average molar ratio of IL-11 to PEG compound attached to the IL-11 is 1:1.

In one aspect of the inventive subject matter, the inventors contemplate a modified interleukin 11 (IL-11) compound that includes an IL-11 polypeptide chain that is covalently coupled to a PEG moiety, wherein the PEG moiety has an average molecular weight of between 10-50 Kd and has distinct first and second PEG portions, wherein the PEG moiety is covalently bound to an N-terminal amino acid, and wherein the IL-11 polypeptide chain is a human or humanized polypeptide chain.

Most typically, the IL-11 polypeptide chain is a human IL-11 polypeptide chain, and/or maybe shortened by deletion of an N-terminal proline. For example, especially suitable IL-11 polypeptide chain may have a sequence according to SEQ ID NO:1. With respect to the PEG moiety it is generally preferred that the moiety has an average molecular weight of 20 Kd or 40 Kd, and/or that the PEG moiety has a Y shape. While not limiting to the inventive subject matter, it is preferred that the molar ratio of polypeptide chain to PEG moiety is about 1:1 (e.g., 0.9:1 to 1:0.9, or 0.8:1 to 1:0.8). In addition, it is contemplated that a second PEG moiety may be covalently coupled to the modified IL-11 via an amino group of the IL-11 polypeptide chain. Furthermore, it is generally preferred that the PEG moiety is covalently bound to the N-terminal amino acid via an amine bond (however, amide bonds are also specifically contemplated).

Viewed from another perspective, the inventors also contemplate a pharmaceutical composition that include a therapeutically effective amount of an IL-11 compound according to the inventive subject matter (e.g., as described above), in combination with a pharmaceutically acceptable carrier. Where desirable, the composition may be formulated for injection, and may include the IL-11 compound is present in an amount to provide a dosage unit of between 10-100 µg/kg for a pediatric or adult patient. Additionally, it is contemplated that the composition may be lyophilized, or in a liquid form for injection or infusion. As best suitable, the pharmaceutical composition may further include a second pharmaceutically active compound, separately, or in admixture with the IL-11 compound. Thus, kits comprising contemplated pharmaceutical compositions together with other components (e.g., second pharmaceutically active compound such as a steroid, an agent that stimulates platelet production in bone marrow, an antibody, an analgesic, or anti-inflammatory agent, or a solvent for reconstitution) are also expressly contemplated herein Consequently, the inventors also contemplate use of an IL-11 compound according to the inventive subject matter in the manufacture of a pharmaceutical composition. While not limiting to the inventive subject matter, especially contemplated treatments include (a) nuclear accident/radiation induced bone and gastrointestinal damage; (b) chemotherapy induced bone and gastrointestinal damage; (c) burn induced thrombocytopenia and gastrointestinal damage; (d) chemotherapy induced thrombocytopenia; (e) trauma-, cancer-, or infection-induced gastrointestinal damage or inflammatory bowel disease, (f) free radical-induced lung damage, and (g) cardiovascular diseases. As noted before, it is generally contemplated that the pharmaceutical composition is formulated for injection and/or that the pharmaceutical composition is lyophilized.

In a further aspect of the inventive subject matter, the inventors therefore also contemplate a method of increasing serum half-life of an interleukin 11 (IL-11) compound. Preferred methods will include a step of covalently coupling an IL-11 polypeptide chain to a PEG moiety, wherein the PEG moiety has an average molecular weight of between 10-50 Kd and has distinct first and second PEG portions, wherein the PEG moiety is covalently bound to an N-terminal amino acid, and wherein the IL-11 polypeptide chain is a human or humanized polypeptide chain. Most typically, the IL-11 polypeptide chain is a human IL-11 polypeptide chain, and/or the IL-11 polypeptide chain is shortened by deletion of an N-terminal proline (e.g., having a sequence according to SEQ ID NO:1).

In further contemplated methods, the PEG moiety has an average molecular weight of 20 Kd or 40 Kd, and/or may have a Y shape. Where desired, the molar ratio of the polypeptide chain to the PEG moiety is about 1:1, and it is further contemplated that the methods may further include a step of covalently coupling a second PEG moiety via an amino group in the IL-11 polypeptide chain. As before, it is contemplated that the PEG moiety is covalently bound to the N-terminal amino acid via an amine bond.

In further contemplated methods, the inventors contemplate a method of treating a condition that is responsive to administration of IL-11. Such methods will typically include a step of administering contemplated pharmaceutical compositions in a therapeutically effective amount to a patient in need thereof. For example, suitable condition may be selected from the group consisting of (a) nuclear accident/radiation induced bone and gastrointestinal damage; (b) chemotherapy induced bone and gastrointestinal damage; (c) burn induced thrombocytopenia and gastrointestinal damage; (d) chemotherapy induced thrombocytopenia; (e) trauma-, cancer-, or infection-induced gastrointestinal damage or inflammatory bowel disease, (f) free radical-induced lung damage, and (g) a cardiovascular disease. Exemplary preferred pharmaceutical composition for these methods may comprise IL-11 I40NY or I20NY, and it is further contemplated that IL-11 is administered (e.g., subcutaneously) in a dosage between 10-100 µg/kg.

Various objects, features, aspects and advantages of the inventive subject matter will become more apparent from the following detailed description of preferred embodiments, along with the accompanying drawing figures in which like numerals represent like components.

DETAILED DESCRIPTION

The inventors have discovered that the type of PEG compound, the location of covalent attachment, and the primary sequence of IL-11 are determinants to the stability and activity of so modified IL-11. In particularly preferred and unexpected aspects, the inventors discovered that IL-11 has substantially improved stability when truncated at the N-terminus by one amino acid that is then PEGylated. Furthermore, the inventors also discovered that the particular type and molecular weight of the PEG moiety is an additional determinant of stability, activity, and toxicity as is further described in more detail below.

Contemplated Compounds

Figures 1, 2:
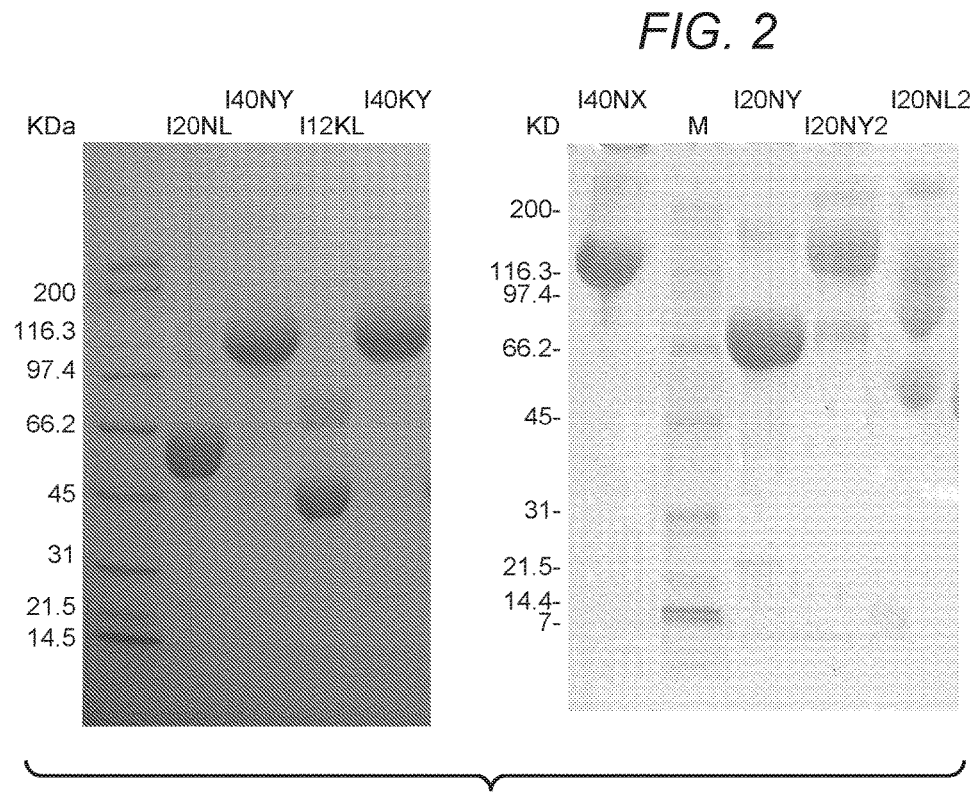
FIG. 1 depicts the primary sequence of IL-11 without N-terminal proline.
FIG. 2 are images of SDS-PAGE gels with molecular weight markers and various PEGylated forms of IL-11 as indicated.

To investigate the influence of type, molecular weight, and attachment position of PEG to IL-11, the inventors prepared various PEGylated IL-11 molecules from recombinant human IL-11 having a primary sequence as shown in FIG. 1 (identical with the native human IL-11 sequence, but lacking the N-terminal proline). It is generally preferred that the IL-11 protein is a N-terminal truncated or modified human IL-11. For example, especially preferred truncated forms include IL-11 molecules that lack at least one or two or three (or more) N-terminal amino acids. Alternatively, the IL-11 may also be modified to have a N-terminal amino acid that is different from the human unmodified counterpart. For example, a modified IL-11 may lack the first N-terminal amino acid and may have a second amino acid that is other than the second amino acid found in unmodified human IL-11 (e.g., lacking P and having G replaced by V). Most typically, N-terminal amino acids will be stabilizing amino acids and therefore especially include M, G, A, S, T, V, or P, and in further contemplated aspects, destabilizing amino acids (e.g., F, Q, N, R, etc.) may be replaced by stabilizing amino acids. Deletions of one or more amino acids from the N-terminal end will typically be limited to the first ten, or the first five, or the first three amino acids. On the other hand, in less preferred aspects, deletions of one, two, three, four, five, or more amino acids may also be implemented at the C-terminus of the IL-11 moiety. As a general guidance, deletions will generally be limited to those that do not or only moderately adversely affect biological activity and/or stability (e.g., loss of activity and/or stability is less than 20%, and more typically less than 10%). Alternatively, or additionally, contemplated IL-11 molecules also include fusion proteins with IL-11 an exemplary fusion proteins include those described in US 2010/0143973, which is incorporated by reference herein. Most typically, the IL-11 is a recombinant protein and may be expressed in a suitable expression system, and most preferably in a prokaryotic system (e.g., *E. coli*) or yeast system (e.g., *Pichia pasteuris*). Of course, it should also be recognized that particularly preferred forms of IL-11 are mature forms (i.e., without leader sequence)

Moreover, it should be appreciated that suitable IL-11 molecules need not be human IL-11 but may be of any other (typically mammalian) origin. Therefore, suitable IL-11 sources (recombinant or native) include primate, murine, porcine, equine, etc. These sequences may then be at least partially humanized to reduce immunogenicity and/or increase stability and/or activity in human. Similarly, synthetic consensus sequences are also contemplated herein.

PEGylation of contemplated IL-11 molecules may be performed in numerous manners and includes covalent as well as non-covalent methods. However, it is generally preferred that the PEGylation uses covalent binding to the IL-11. There are numerous manners known in the art to covalently attach a PEG group to a protein and suitable methods include those that react the N-terminal amino group or the C-terminal carboxylic acid group with a suitable reactive group on the PEG moiety (e.g., aldehyde, maleimide, acid chloride, etc.), or sulfhydryl reactive groups (e.g., maleimide, pyridyl disulfide, vinyl sulfone, etc.) that allow for disulfide bonding to cysteine groups, or amino reactive reagents that react with an ε-amino group of a lysine amino acid (e.g., NHS-esters, NHS-carbonates, triazine, groups, etc). Therefore, it is also contemplated that one or more amino acids may be added to the N- and/or C-terminus to introduce a reactive group suitable for attachment of a PEGylation group. For example, serine or threonine may be added to allow for enzymatic attachment using a N-actylgalactosamine or PEG sialic derivative, or a lysine for covalent attachment to the ε-amino group, or a phenyl alanine or threonine group for attachment to a hydroxyl group.

With respect to suitable PEG molecules for use herein, it is generally contemplated that various molecular weights for PEG are appropriate, and contemplated molecular weights are between 2 Kd and 200 Kd (average or nominal molecular weight). However, particularly preferred molecular weights (average or nominal molecular weight) include those between 10-50 Kd per linear chain in a PEGylation moiety. Moreover, it is generally preferred that the PEG moiety will have a single linear, or Y-shaped PEG moiety, and even more preferably that such PEG moiety will have a molecular weight of between 20-40 Kd. Alternatively, suitable PEG moieties may also include dendrimeric PEG constructs, as well as PEG moieties with more than two linear chains. Where the PEG moieties have more than one linear PEG chain, it is generally preferred that the chains have an average molecular weight that is substantially the same (average molecular weight difference less than 15%).

In further preferred aspects, the PEG moiety is covalently attached to the IL-11 via the N-terminal amino group of IL-11 and/or (optionally) to an ε-amino group of an internal lysine or the ring nitrogen of histidine. Due to the N-terminal covalent bond, it is preferred that the molar ratio of IL-11 to PEG moiety is about 1:1 (e.g., 0.9:1 to 1:0.9, or 0.8:1 to 1:0.8, etc.). In addition, it should be appreciated that moderate levels of PEGylation may be present at internal amino acid residues (e.g. between 10%-20%, or between 1%-10% of all IL-11 may carry an extra PEGylated internal amino acid). For example, a second PEG moiety may be attached to an ε-amino group of an internal lysine or histidine. As is further shown in more detail below, a particularly preferred form of PEGylated IL-11 is I40NY, comprising human IL-11 (lacking N-terminal proline), to which is attached on the N-terminus a Y-shaped PEG moiety with an average molecular weight of 40 Kd.

In still further alternative aspects, it should be appreciated that the PEGylation may be mixed with respect to the attachment position of the PEG moiety and/or kind of attachment. Therefore, IL-11 may be subjected to random non-covalent PEGylation and site specific PEGylation at an N-terminal amino acid, or subjected to different site specific PEGylations at the N-terminal amino acid and an internal amino acid. For example, and most preferably, IL-11 (or any modified form thereof) may be PEGylated at the N-terminal amino acid and optionally at an internal amino acid via a nitrogen atom (e.g., from lysine or histidine) in addition to the N-terminal modification.

For example, and using the truncated IL-11 as shown FIG. 1, the inventors performed PEGylation using the PEG reagents as shown in Table 1 (where n and m are independently an integer between 80 and 1000, depending on the molecular weight of the compound) following experimental protocol as provided by the manufacturer and as described in more detail further below.

TABLE 1

| Manufacturer/ Cat. No. | Structure/Molecular size |
|---|---|
| NOF/ SUNBRIGHT ME-200AL | $H_3CO-(CH_2CH_2O)_n-CH_2-CH_2-\overset{\overset{O}{\|\|}}{CH}$ <br> 20 KD |
| Jenkem/ Y-PLAD-40K | $\begin{array}{c} H_3CO-(CH_2CH_2O)_n-CH_2-CH_2 \\ \phantom{xxxxxxxxxxxxxxxxxxxxxxx} \diagdown \\ \phantom{xxxxxxxxxxxxxxxxxxxxxxxxxx} N-CH_2-\overset{\overset{O}{\|\|}}{C}-NH-C_2H_4-\overset{\overset{O}{\|\|}}{CH} \\ \phantom{xxxxxxxxxxxxxxxxxx} \diagup \\ H_3CO-(CH_2CH_2O)_n-CH_2-\underset{\underset{O}{\|\|}}{C} \end{array}$ <br> 40 KD |
| NOF/ SUNBRIGHT ME-120TS | $H_3CO-(CH_2CH_2O)_n-\overset{\overset{O}{\|\|}}{C}-O-N\begin{pmatrix}\text{succinimidyl}\end{pmatrix}$ <br> 12 KD |
| NOF/ SUNBRIGHT GL2-400TS | $\begin{array}{c} H_3CO-(CH_2CH_2O)_n-CH_2 \\ \phantom{xxxxxxxxxxxxxxxxx} \| \\ H_3CO-(CH_2CH_2O)_n-CH \\ \phantom{xxxxxxxxxxxxxxxxx} \| \\ \phantom{xxxxxxxxxxxxxxxxxx} H_2C-O-\overset{\overset{O}{\|\|}}{C}-O-N\begin{pmatrix}\text{succ}\end{pmatrix} \end{array}$ <br> 40 KD |
| NOF/ SUNBRIGHT GL2-200AL3 | $\begin{array}{c} H_3CO-(CH_2CH_2O)_n-CH_2 \\ \phantom{xxxxxxxxxxxxxxxxx} \| \\ H_3CO-(CH_2CH_2O)_n-CH \\ \phantom{xxxxxxxxxxxxxxxxx} \| \\ \phantom{xxxxxxxxxxxxxxxxxx} H_2C-O-\overset{\overset{O}{\|\|}}{C}-NH-C_2H_4\overset{\overset{O}{\|\|}}{CH} \end{array}$ <br> 20 KD |

TABLE 1-continued

| Manufacturer/Cat. No. | Structure/Molecular size |
|---|---|
| NOF/SUNBRIGHT ME-050TS | $H_3CO-(CH_2CH_2O)_n-C(=O)-O-N$(succinimide)<br>5 KD |
| NOF/SUNBRIGHT GL4-400AL3 | [branched PEG structure with four $H_3CO-(CH_2CH_2O)_n-$ arms connected through $-(CH_2CH_2O)_m-$ linkers to a central $H_2C-O-C(=O)-NH-C_2H_4-CH(=O)$ group]<br>40 KD |

After PEGylation of the truncated IL-11, the so obtained compounds were purified as also addressed in more detail below, and the various PEGylated IL-11 molecules had the following designations as shown in Table 2:

TABLE 2

| Compound code | PEG size/KDa | Structure of PEG | Conjugation site (bonding) |
|---|---|---|---|
| I20NL | Single 20 | linear | N-terminal (amine bond) |
| I40NY | Single 40 | Y-shaped | N-terminal (amine bond) |
| I12KL | Single 12 | linear | N-terminal (amide bond) |
| I40KY | Single 40 | Y-shaped | N-terminal (amide bond) |
| I20NY | Single 20 | Y-shaped | N-terminal (amine bond) |
| I20NL2 | 20 × 1~3 | linear | N-terminal/lysine or histidine (amine bond) |
| I20NY2 | 20 × 1~3 | Y-shaped | N-terminal/lysine or histidine (amine bond) |
| I05KL4 | 5 × 4~5 | Linear | N-terminal/lysine/histidine (amide bond) |
| I40NX | Single 40 | 4-arm | N-terminal (amine bond) |

Most notably, the inventors have discovered that the type of PEG moiety and the site of attachment (and to some degree the sequence of the IL-11) had unexpected and substantial influence on biological activity and stability in vivo. As is more evident from the experimental data below, especially preferred PEGylations are at the N-terminal amino acid using a single Y-shaped PEG moiety, particularly where the IL-11 was truncated.

Contemplated Compositions

Based on the inventors' discovery of extended biological activity of contemplated compounds, it is generally contemplated that the compounds according to the inventive subject matter may be formulated for treatment of various diseases associated with a lack of IL-11 or characterized by a therapeutic response to treatment with IL-11. Therefore, and among other contemplated uses, the inventors especially contemplate that pharmaceutical compositions comprising contemplated compounds may be effective for the treatment or prevention of (a) chemotherapy-induced thrombocytopenia, (b) nuclear accident/radiation induced bone and gastrointestinal (GI) damage; (c) chemotherapy induced bone and GI damage; (d) burn induced thrombocytopenia and GI damage; (e) other causes of thrombocytopenia; (f) other causes of GI damage, including inflammatory bowel diseases like Crohn's Disease and ulcerative colitis, as well as pseudomembraneous colitis, (g) free radical-induced lung damage, and/or (h) cardiovascular diseases, wherein contemplated pharmaceutical compositions comprise a therapeutically effective amount of contemplated compounds (or pharmaceutically acceptable salt, hydrate, or prodrug thereof), and a pharmaceutically acceptable carrier. For example, in one aspect of the inventive subject matter, contemplated compositions are formulated for treatment of chemotherapy-induced thrombocytopenia or GI damage or radiation induced bone and gastrointestinal (GI) damage. Alternatively, or additionally, it should also be appreciated that contemplated compositions may be formulated to induce acute phase proteins, and/or to modulate antigen-antibody responses.

It is particularly preferred that contemplated compounds are included in a composition that is formulated with one or more non-toxic pharmaceutically acceptable carriers. Suitable pharmaceutical compositions are preferably formulated for injection or infusion, or for oral administration in solid or liquid form. Thus, it should be appreciated that pharmaceutical compositions according to the inventive subject matter may be administered to humans and other (typically mammalian) animals using various routes, including parenterally, orally, intraperitoneally, and topically.

For example, suitable pharmaceutical compositions for injection preferably comprise pharmaceutically acceptable sterile aqueous or nonaqueous solutions, dispersions, emulsions, or suspensions, as well as sterile powders for reconstitution into sterile injectable solutions or dispersions prior to use. Examples of suitable aqueous and nonaqueous carriers, diluents, solvents, or vehicles include water, Ringer's solution, and isotonic sodium chloride solution, ethanol, polyols (e.g., glycerol, propylene glycol, polyethylene glycol, etc.), and suitable mixtures thereof, oils, and injectable organic esters (e.g., ethyl oleate). Contemplated compositions may also contain various inactive ingredients, including preservatives, wetting agents, emulsifying agents, and/or dispersing agents. Sterility may be ensured by inclusion of antibacterial and/or antifungal agents (e.g., paraben, phenol sorbic acid, chlorobutanol, etc.), as well as by filtration across sub-micron membranes (e.g., 0.45 µM or 0.22 µM pore size), autoclaving or pasteurizing, and radiation (e.g., gamma or e-beam). Where appropriate, osmotically active agents may be included (e.g., sugars, sodium chloride, etc.). While not limiting to the inventive subject matter, contemplated formulations for injection are typically in a pH range of 3-9, more typically 6-8, and most typically 7.4+/−0.3. Of course, it should also be recognized that all liquid formulations may be preserved in various manners to facilitate long-term storage/stockpiling. For example, contemplated manners of stabilization include water/solvent removal using lyophilization, spray-drying, crystallization, adsorption on (preferably biocompatible or pharmaceutically acceptable) solid phases, etc.

The compositions according to the inventive subject matter may be administered using various routes, including orally, parenterally, by inhalation, topically, rectally, nasally, or via an implanted reservoir, wherein the term "parenteral" as used herein includes subcutaneous, intravenous, intramuscular, intraarticular, intrasynovial, intrathecal, intrahepatic, intralesional, and intracranial administration (typically injection or infusion). Preferably, the compositions are administered via injection, typically intravenously, and more preferably subcutaneously. Contemplated pharmaceutical compositions may also be administered topically, especially when the target of treatment includes areas or organs readily accessible by topical application, including diseases of the eye, the skin, the lower intestinal tract, or areas exposed during surgical intervention. There are numerous topical formulations known in the art, and all of such formulations are deemed suitable for use herein.

With respect to the amount of contemplated compounds in the composition, it should be recognized that the particular quantity will typically depend on the specific formulation and desired purpose. Therefore, it should be recognized that the amount of contemplated compounds will vary significantly. However, it is generally preferred that the compounds are present in a minimum amount effective to deliver a therapeutic effect in vitro and/or in vivo.

Thus, in most preferred embodiments, contemplated compounds will be present in an amount of between about 0.1 µg/ml to about 100 mg/ml, more typically in an amount of between about 10 µg/ml to about 10 mg/ml, and most typically between about 5 µg/ml to about 100 µg/ml. With respect to a dosage unit, it is generally contemplated that contemplated compounds are administered at a dosage effective to achieve a desired therapeutic effect, typically 10-100 µg/kg, and more preferably 30-70 µg/kg. However, alternate dosage units may be between 0.1-10 µg/kg, or 50-80 µg/kg, or 80-120 µg/kg, or 120-200 µg/kg, or even higher. Viewed from a different perspective, it should be appreciated that a single-use unit of contemplated formulations may include between about 0.3 mg to 3.0 mg of PEGylated IL-11, or between about 3 mg to 7 mg of PEGylated IL-11, or between about 7 mg to 10 mg of PEGylated IL-11 (most typically with a specific activity of $7-9\times10^6$ U/mg). Unless the context dictates the contrary, all ranges set forth herein should be interpreted as being inclusive of their endpoints, and open-ended ranges should be interpreted to include commercially practical values. Similarly, all lists of values should be considered as inclusive of intermediate values unless the context indicates the contrary.

In addition, it should be noted that contemplated formulations may include one or more additional pharmaceutically active agents, which may be present in the same formulation, or be separately made available (in a different type of formulation or the same), or be sold as a kit. For example, suitable additional pharmaceutically active agents include various steroids (e.g., corticosteroids), agents that stimulate platelet production in bone marrow (e.g., $Li_2CO_3$, folic acid, etc.), antibodies, analgesics, and anti-inflammatory agents.

Contemplated Uses

Contemplated compounds may be particularly useful as therapeutic agents for single or combination use in the treatment of (a) nuclear accident/radiation induced bone and gastrointestinal (GI) damage; (b) chemotherapy induced bone and GI damage; (c) burn induced thrombocytopenia and GI damage; (d) other causes of thrombocytopenia; (e) other causes of GI damage, including inflammatory bowel diseases like Crohn's Disease and ulcerative colitis, as well as pseudomembraneous colitis, (f) free radical-induced lung damage, and (g) cardiovascular diseases.

Consequently, the inventors also contemplate use of the compounds presented herein for the manufacture of a drug for treatment of (a) nuclear accident/radiation induced bone and GI damage; (b) chemotherapy induced bone and GI damage; (c) burn induced thrombocytopenia and GI damage; (d) other causes of thrombocytopenia; (e) other causes of GI damage, including inflammatory bowel diseases like Crohn's Disease and ulcerative colitis, as well as pseudomembraneous colitis, (f) free radical-induced lung damage, and (g) cardiovascular diseases.

Viewed from another perspective, the inventors also contemplate methods of treatment of (a) nuclear accident/radiation induced bone and GI damage; (b) chemotherapy induced bone and GI damage; (c) burn induced thrombocytopenia and GI damage; (d) other causes of thrombocytopenia; (e) other causes of GI damage, including inflammatory bowel diseases like Crohn's Disease and ulcerative colitis, as well as pseudomembraneous colitis, (f) free radical-induced lung damage, and (g) cardiovascular diseases in a human in need thereof in which contemplated compounds are administered at a therapeutically effective dosage.

Experiments and Experimental Data

Materials: Purified bulk of recombinant human IL-11, derived from yeast was provided by Hangzhou Jiuyuan Gene Engineering Company (Lot#20121005/1006/1007/1008). 7TD1 murine hybridoma cell line, was acquired from DSMZ (No. ACC 23). Paraplatin® injection (generic name: carboplatin) 10 mg/mL (Lot: 5A03935) was manufactured by Bristol-Myers Squibb Company. Trypsin of sequencing grade, modified from bovine pancreas (Cat. No. 11418025001) was purchased from Roche diagnostics. Mouse IL-11 receptor alpha was acquired from MyBioSource, Inc. (Cat. No. MBS553276). CellTiter 96® Aqueous Non-Radioactive Cell Proliferation Assay (MTS) (Cat. No. G5430) was purchased from Promega for 7TD1 cell assay. The DuoSet ELISA development kit for Human IL-11 was purchased from R&D Systems Inc. (Cat. No. DY218). The Purification resin-MacroCap SP (Product code 17-5440-01) was acquired from GE Healthcare Life Sciences. The Precise Tris-Glycine 8-16% polyacrylamide gels were purchased from Thermo Scientific. Trifluoroacetic acid (Cat.

No. 302031) and acetonitril (Cat. No. 34967) for HPLC use were purcahsed from Sigma-Aldrich.

Monofunctional PEG of various forms with Cat. No. SUNBRIGHT® ME-120TS, ME-200AL, GL2-400TS, ME-050TS, GL4-400AL3, GL2-200AL3, were purchased from NOF Corporation, and Y-PALD-40K was purchased from Jenkem Technology USA. Molecular structures of the PEG reagents were shown above in Table 1.

Preparation of I12KL/I40KY/I05KL4: 5 mg/mL protein was introduced with mixture of 1 to 2-fold molar ratio of respective PEG reagent (NOF/SUNBRIGHT ME-120TS for I12KL; SUNBRIGHT GL2-400TS for I40KY) and 50 mM $NaHCO_3$ at pH about 8. I05KL4 (PEG reagent: NOF/SUNBRIGHT ME-120TS) was prepared with the same manner except the molar ratio of PEG to protein was added at 12-fold. The reaction mixture was incubated at room temperature for 2 hours, followed by quenching with 2 mM glycine. PEGylated product was isolated using chromatographic purification procedures as followed. The PEG molecule was linked to protein by amide bonding.

Preparation of I20NL/I40NY/I20NY/I20NL2/I20NY2/I40NX: 5 mg/mL protein was introduced with mixture of 1 to 2-fold molar ratio of respective PEG reagent (NOF/SUNBRIGHT ME-200AL for I20NL and I20NL2; Jenkem/Y-PLAD-40 for I40NY; NOF/SUNBRIGHT GL2-200AL3 for I20NY and I20NY2; NOF/SUNBRIGHT GL4-400AL3 for I40NX), 10 mM sodium cyanoborohydride and 50 mM $NaH_2PO_4$. For conjugating onto two sites, the molar ratio of PEG was added at 3.5 to 5.5-fold. The pH was adjusted to about 4.5-5.0. The reaction mixture was incubated at room temperature for 24 hours, followed by quenching with 2 mM glycine. The PEG molecule was linked to protein by a more stable amine bonding. PEGylated product was isolated using chromatographic purification as followed.

Chromatographic Purification: The pH of protein solution was adjusted to 4-5 with 1M acetic acid, followed by centrifugation or filtration to remove particulates. Four volumes of water was introduced. For conjugate containing PEG over 20 KDa: The protein solution was loaded onto a MacroCap SP column (1×6 cm) that was equilibrated with buffer A containing 20 mM sodium acetate pH 5. The protein was eluted with gradient- or step-elution of buffer B, containing 20 mM sodium acetate pH 5 and 1M NaCl. For conjugate containing PEG below 20 KDa: The protein solution was loaded onto a MacroCap SP column (1×6 cm) that was equilibrated with buffer A containing 20 mM sodium phosphate pH 7. The protein was eluted with gradient- or step-elution of buffer B, containing 20 mM sodium phosphate pH 7 and 1M NaCl. A typical final product as analyzed in a SDS PAGE gel can be seen in FIG. 2. Here, the left lane was loaded with molecular weight markers, and various PEGylated forms of IL-11 were loaded into the remaining lanes. Note that I40NY ran at an apparent molecular weight of over 100 Kd, bigger than the estimated one of 60 Kd, which is likely due to the Y-shaped of its PEG moiety. In further particularly preferred aspects, purification of contemplated compounds is performed as a one-step purification process, which provides added advantages in a downstream scale-ups.

Purity Check by RP-HPLC: The content of each PEGamer was analyzed by reverse-phase (RP) chromatography employing the UPLC coupled with diode-array detector-UltiMate 3000 Rapid Separation LC Systems from Thermo Scientific. The chromatographic procedure was carried out using: Column: Acquity C18, 1.7 μm, 2.1×150 mm, 300 Å pore size, equipped with a guard cartridge; Mobile phase A: 0.1% (v/v) TFA in 50% (v/v) acetonitrile; Mobile phase B: 0.1% (v/v) TFA in 95% (v/v) acetonitrile; Flow rate: 0.4 ml/min; Column temperature: 65° C.; Detection: 214 nm; Inject 20 μg and run gradient as in Table 3 below

TABLE 3

| Time (min) | A % | B % |
|---|---|---|
| 0 | 100 | 0 |
| 2 | 100 | 0 |
| 9.9 | 80 | 20 |
| 9.95 | 0 | 100 |
| 11.3 | 0 | 100 |
| 11.31 | 100 | 0 |
| 17.5 | 100 | 0 |

Determination of Protein Content: The protein content was determined by the UV/Vis microplate and cuvette spectrophotometer—Multiskan GO from Thermo Scientific. Extinction coefficient in units of $M^{-1}$ $cm^{-1}$, at 280 nm measured in water is 17,990. Alternatively protein concentration is directly determined by ultraviolet spectroscopy at wavelength 280 nm, using the absorbency value of 0.944 for a 0.1% (1 mg/ml) solution. Protein quantitation using absorbance at 280 nm measures the absorbance of aromatic amino acids such as tryptophan and tyrosine, leaving PEG moiety undetected. As a result, protein concentration by weight stated herein does not contain PEG molecule.

Pharmacokinetics (PK) study in healthy rats: The in vivo manipulation was carried out in 3 male Sprague-Dawley rats following single dose administration of contemplated compounds by intravenous or subcutaneous route at a dosing level of 100-150 μg/kg. Blood samples were collected in numerous time points in heparin tubes, followed by plasma separation and storage at −20° C. The concentration of immunoreactive IL-11 in plasma samples were determined by the DuoSet ELISA kit for Human IL-11 (R&D Systems Inc. Cat. No. DY218). The parameters of pharmacokinetics were yielded by the WinNonlin 5.3 software using non-compartment model.

Pharmacodynamics (PD) study in healthy rats: The pharmacodynamics assessment was carried out in 4 male Sprague-Dawley rats using intravenous or subcutaneous administration of respective contemplated compounds at dosing strength of 100-150 μg/kg. Blood samples were collected in numerous time points in heparin tubes, followed by plasma separation and storage at −20° C. The blood cell count was carried out on a Cell-DYN 3500 hematology analyzer.

Pharmacodynamics (PD) study in myelosuppressive rats: The pharmacodynamics assessment was carried out in 4 male Sprague-Dawley rats, using intravenous administration of carboplatin at 40 mg/kg on Day 0 to induce myelosuppression. Contemplated compounds were subcutaneously injected on Day 1 at 150 μg/kg. Blood samples were collected in numerous time points in heparin tubes, followed by plasma separation and storage at −20° C. The blood cell count was carried out on a Cell-DYN 3500 hematology analyzer.

Tryptic mapping: The reaction solution was prepared in 50 mM Tris pH 8.3 buffer containing 2 mg/mL protein and 1/50 (W/W) trypsin. Incubated at room temperature for 6 hours, followed by adding equal volume of 0.2% TFA (trifluoroacetic acid) solution. Any particulate matters were removed by centrifuge prior injection onto HPLC. The chromatographic procedure was carried out using: Column: Zorbax 300 SB-C8, 2.1×150 mm, 5 μm, 300 Å pore size;

Mobile phase A: 0.1% (v/v) TFA; Mobile phase B: 0.1% (v/v) TFA in 95% (v/v) acetonitrile; Flow rate: 0.2 ml/min; Detection: 214 nm; Inject 10 µg and run gradient as in Table 4 below.

TABLE 4

| Time (min) | A % | B % |
|---|---|---|
| 0 | 100 | 0 |
| 3 | 100 | 0 |
| 8 | 95 | 5 |
| 45 | 55 | 45 |
| 45.1 | 0 | 100 |
| 52 | 0 | 100 |
| 52.1 | 100 | 0 |
| 65 | 100 | 0 |

The identification of proteolytic peptide was carried out with HPLC coupled with MS spectrometry (Thermo LCQ Advantage).

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

Figure 3:
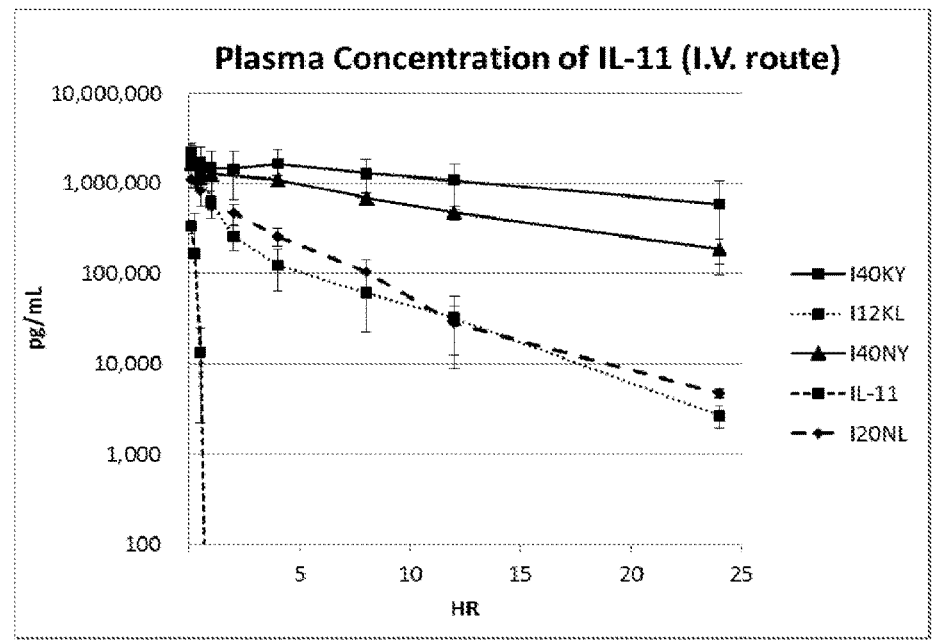
FIG. 3 is a graph depicting plasma concentrations of various IL-11 compositions after single i.v. administration.

While it is generally known that PEG can impart the plasma stability of its conjugates, it is not predictable what attachment type, chain length, and molecular structure will produce a specific result with respect to therapeutic effect and/or pharmacologic parameter. In a first example, the truncated IL-11 conjugates of various PEG size were investigated with regard to plasma stability in normal rats. After intravenous administration, the observed plasma half-life of un-PEGylated IL-11 was found to be very short, less than 10 minutes as compared to those (3.5-13.7 hr) of its PEGylated counterparts. Among the latter, higher molecular-weight PEG imparted greater plasma stability in the following order: I40KY (13.7 hr)~I40NY (8.5 hr)>I20NL (3.8 hr)~I12KL (3.5 hr). FIG. 3 illustrates the plasma concentration of the various forms of PEGylated IL-11 after single intravenous administration. Each sample was dosed at 100 µg/kg in rats. It was concluded that in this example larger or longer PEG chain resulted in longer serum half-life.

Figure 4:
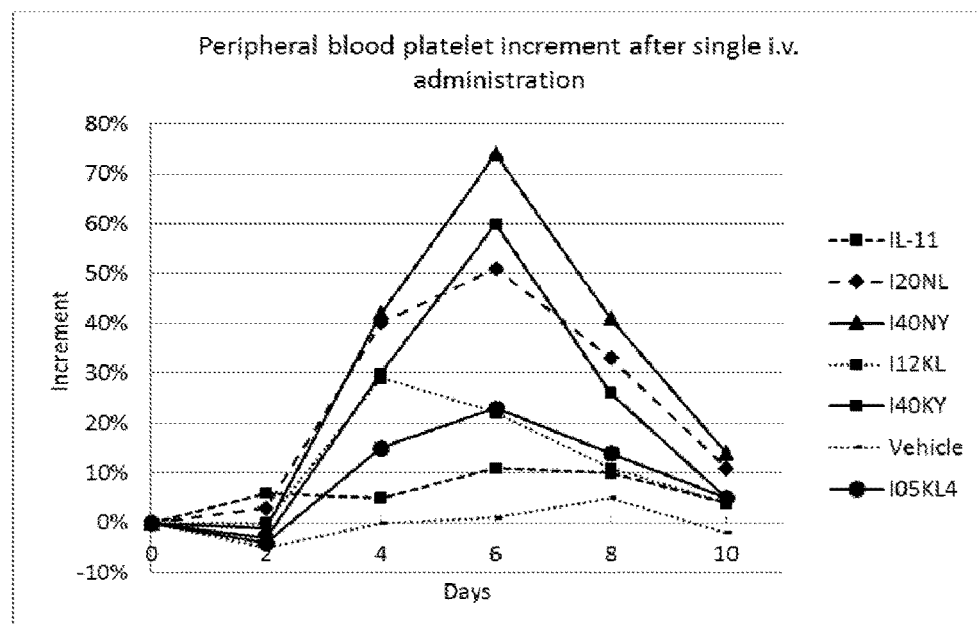
FIG. 4 is a graph depicting platelet increment after single i.v. administration of various IL-11 compositions.

In a second example, pharmacodynamics assessment was carried out with healthy Sprague-Dawley rats following intravenous route measuring platelet increment after single intravenous administration at 100 µg/kg. As can be seen, from FIG. 4, 40-KD conjugates (I40NY and I40KY) induced more platelet increment (60-75%) than I20NL (50%), where Y represented the Y-shape PEG and L the linear shape PEG. The results also suggested multiple conjugation (I05KL4, 5-KD PEG conjugated on four sites) to be less effective than a single long PEG chain on the N-terminus, as multiples with shorter PEG conjugates had only limited efficacy at about 25% of platelet increment. It was concluded in this example that longer PEG chain on single site resulted in a higher efficacy in the respect of platelet induction. This appears to be opposite to the effect of PEGylation on recombinant human growth hormone.

Figure 5:
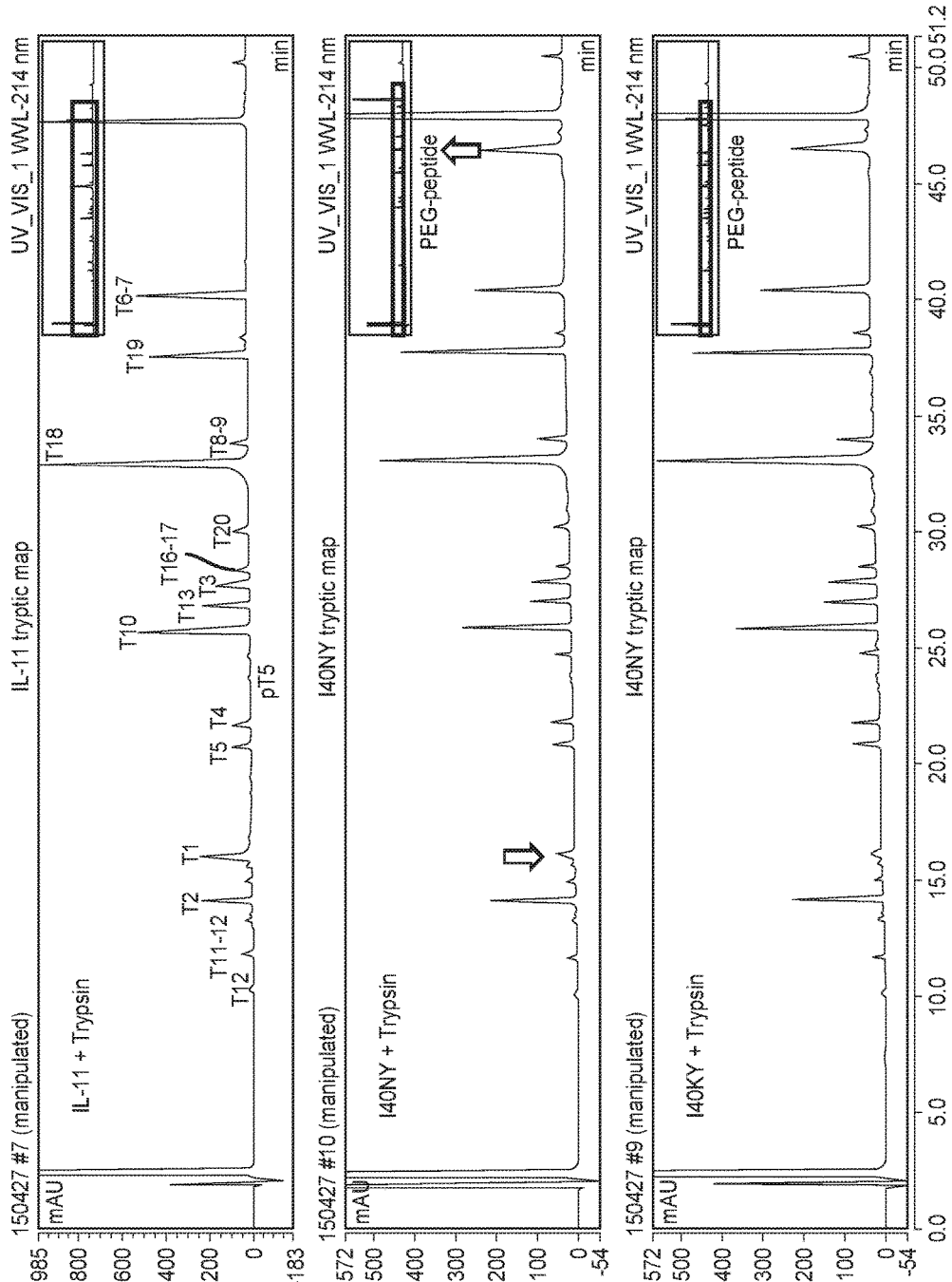
FIG. 5 depicts chromatograms of peptide maps for tryptic digestion of unconjugated IL-11, I40NY and I40KY in comparison.

In a third example, conjugation sites were investigated by tryptic mapping, coupled with LC/MS identification of proteolytic peptides. FIG. 5 depicts tryptic maps of IL-11 (unconjugated), I40NY, and I40KY, and Table 5 below provides the tryptic peptides.

TABLE 5

| Mass | Position | Peptide # | Peptide Sequence |
|---|---|---|---|
| 773.9 | 1-8 | T1 | GPPPGPPR |
| 669.7 | 9-14 | T2 | VSPDPR |
| 1217.4 | 15-25 | T3 | AELDSTVLLTR |
| 774.9 | 26-32 | T4 | SLLADTR |
| 798.9 | 33-39 | T5 | QLAAQLR |
| 261.3 | 40-41 | T6 | DK |
| 3319.8 | 42-74 | T7 | FPADGDHNLDSLPTLAMSAGALGALQLPGVLTR |
| 287.4 | 75-76 | T8 | LR |
| 950.1 | 77-84 | T9 | ADLLSYLR |
| 839.0 | 85-90 | T10 | HVQWLR |
| 174.2 | 91-91 | T11 | R |
| 618.7 | 92-98 | T12 | AGGSSLK |
| 1327.5 | 99-110 | T13 | TLEPELGTLQAR |
| 402.5 | 111-113 | T14 | LDR |
| 400.5 | 114-116 | T15 | LLR |
| 174.2 | 117-117 | T16 | R |
| 860.1 | 118-124 | T17 | LQLLMSR |
| 2600.0 | 125-150 | T18 | LALPQPPPDPPAPPLAPPSSAWGGIR |
| 1914.2 | 151-168 | T19 | AAHAILGGLHLTLDWAVR |
| 655.9 | 169-174 | T20 | GLLLLK |
| 275.3 | 175-176 | T21 | TR |
| 131.2 | 177-177 | T22 | L |

Here it can be seen that the peak corresponding to the T1 peptide was noticeably reduced in the tryptic maps of I40NY and I40KY. This indicates that both conjugates with PEG were linked onto T1 peptides, where the N-terminal amine was the only site for the chemical conjugation. As a result, I40NY and I40KY were both N-terminally linked, however only differed in chemical bonding with amine bond for I40NY and amide bond for I40KY. Notably, both I40NY and I40KY exhibited similar effects in serum half-life and platelet induction via intravenous administration.

Figure 6:
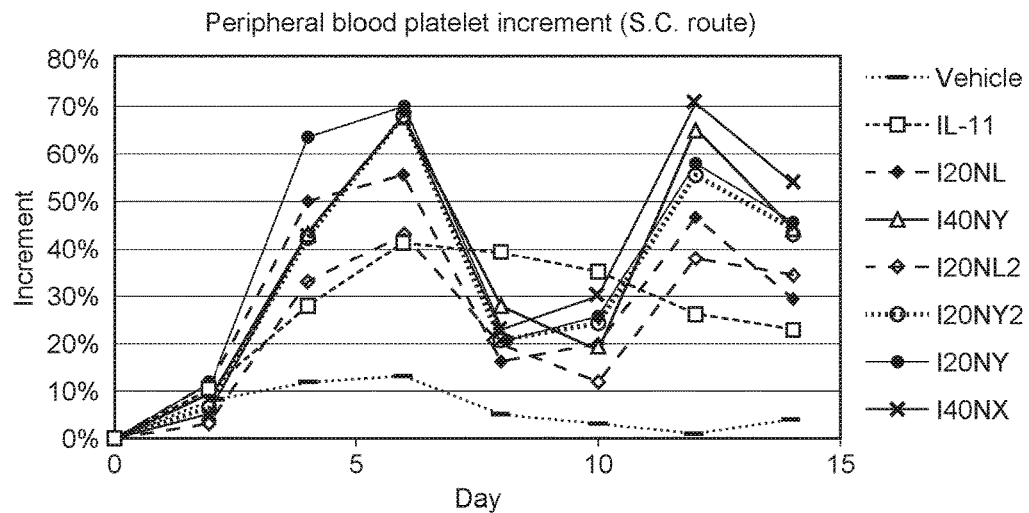
FIG. 6 is a graph depicting platelet increment after s.c. administration of various IL-11 compositions (Daily injection for IL-11 in consecutive 14 days; and weekly injection for PEGylated counterparts).

Since an amine bond is more stable than an amide bond, and yield of mono-PEGylated product was more homogeneous for selective PEGylation using reductive amination, in the next study, various N-terminal conjugates were investigated in terms of efficacy in platelet production, and were evaluated by their respective associated side-effect via subcutaneous administration in healthy rats. FIG. 6 depicts results of a pharmacodynamics study of six PEGylated IL-11 conjugates in rats with subcutaneous administration at 150 μg/kg. IL-11 was administered daily for continuous 14 days while PEGylated IL-11 were injected once weekly. PEG shape can influence the function of the conjugate. Particularly, the non-linear shape PEG molecule imparts better plasma stability and more potency than its linear counterpart. As displayed in FIG. 6, I20NY induced more platelet increment (58-70%) than I20NL (46-55%), where Y represented the Y-shape PEG and L the linear shape PEG. These results suggested that a Y-shaped PEG had a greater effectiveness than the linear form of the same molecular weight. However, I40NY (Y-shape) and I40NX (4-arm comb-shape) were comparable in platelet production as both increased up to about 65-70%, suggesting the influence of PEG shape became saturated when the PEG size was about or over 40KD. Notably, double PEGylation of the same PEG length reduced the in vivo efficacy, as I20NL2 (linear PEG onto two sites) and I20NY2 (Y-shaped PEG onto two sites) had lower platelet production than their single PEGylated counterparts. It was therefore concluded that I40NY, I40NX and I20NY exerted higher efficacy among various N-terminal conjugated IL-11s. Moreover, it was noted that the effect of second administration was somehow down-regulated for smaller PEG conjugates such as 20-KD PEG regardless of number of conjugation site. As a result, I40NY and I40NX were unexpectedly effective compounds with desirable biological properties and relatively moderate adverse effects (especially plasma expansion). Moreover, the biological data further suggest that the so modified IL-11 compounds can be administered less frequently, and most preferably twice weekly, once weekly, or even less. Such schedule is particularly relevant where contemplated compounds are employed in the treatment of thrombocytopenia in a large population (e.g., exposed to radiologic exposure).

Figure 7:
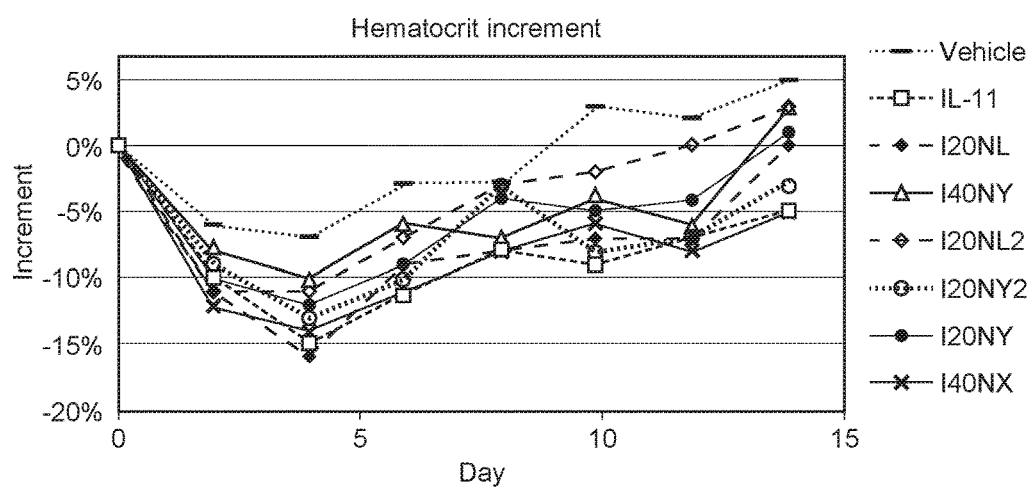
FIG. 7 is a graph depicting hematocrit reduction after s.c. administration of various IL-11 compositions (Daily injection for IL-11 in consecutive 14 days; and weekly injection for PEGylated counterparts).
Figure 8:
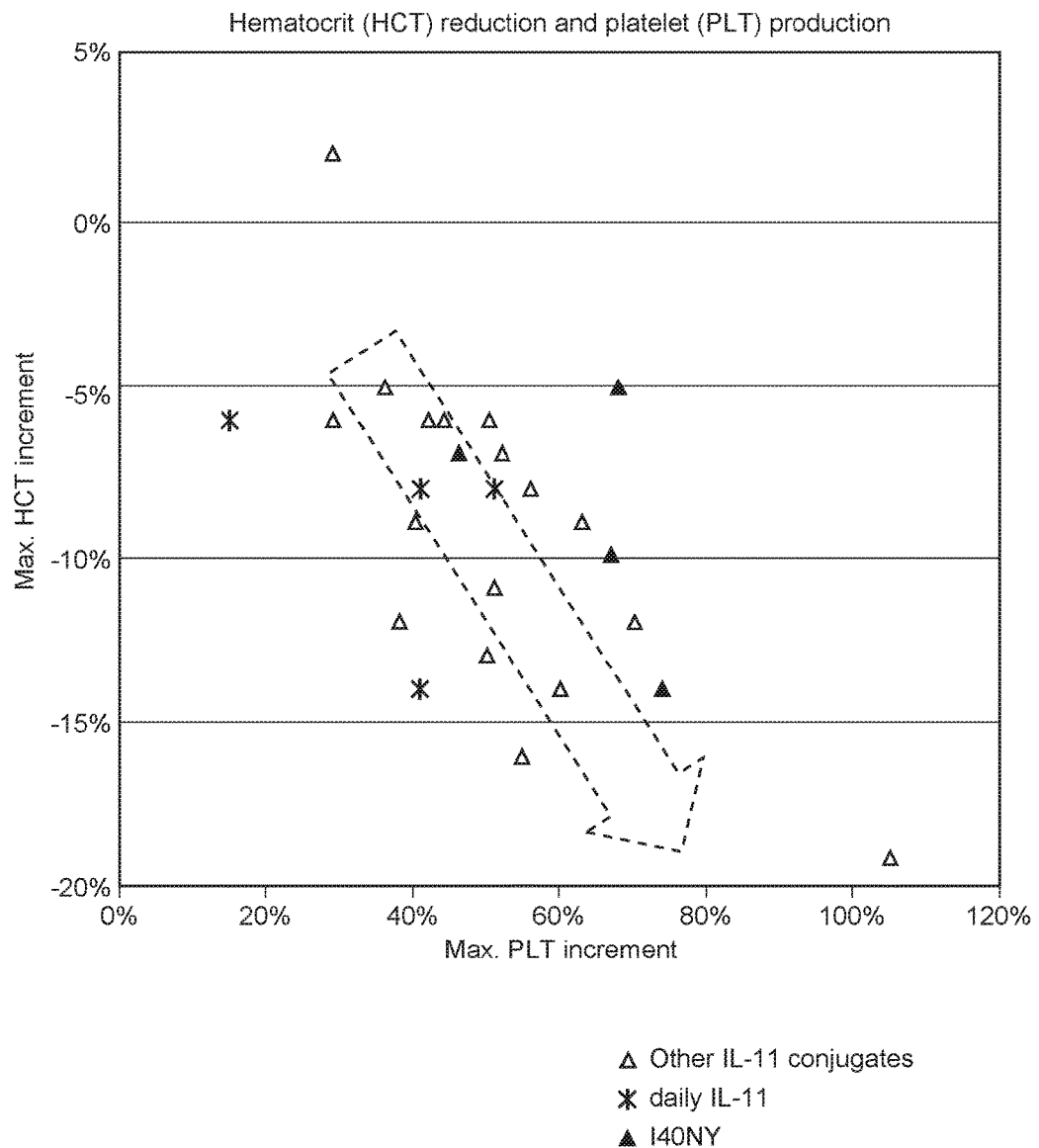
FIG. 8 is a graph suggesting a correlation between maximal platelet induction and maximal reduction of hematocrit.

The inventors also studied the side-effect associated with IL-11 conjugates in healthy rats. Hematocrit status is usually used as a marker for assessment of side-effect in clinical use of IL-11, because patients might experience dilutional anemia due to plasma expansion. In the animal study, IL-11 was administered subcutaneously for continuous 14 days at 150 μg/kg while PEGylated IL-11 were injected once weekly at the same dose. As shown in FIG. 7, all drugs resulted in decreased hematocrit but I40NY was found to have less reduction while maintained higher activity than the rest of PEGylated conjugates. The mitigated dilutional anemia of dosing with I40NY is more prominent when compared in the same chart with other individual animal experiments using conjugated and unconjugated IL-11s. A correlation between platelet production and side-effect as manifested by reduction of hematocrit was established in FIG. 8, suggesting a trend of intensifying side-effect along with the increasing and dose-dependent efficacy when various modified and unmodified IL-11s were plotted in the chart. I40NYs, at different doses, were distinctly located on the right upper side of the trend, indicating less plasma expansion than some other compounds and unmodified IL-11 on the basis of comparable efficacy. In terms of product characterization, the inventors characterized physicochemical and pharmacological properties of a preferred compound, I40NY.

Figure 9:
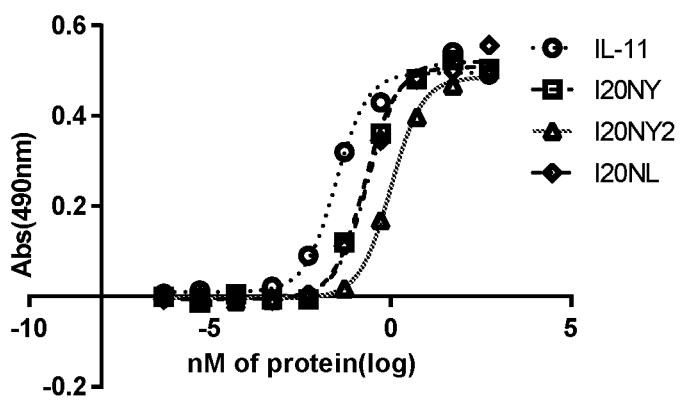
FIG. 9 are graphs depicting cell proliferation activity of PEGylated compounds in 7TD1 assays, in comparison to unconjugated IL-11.
Figure 9:
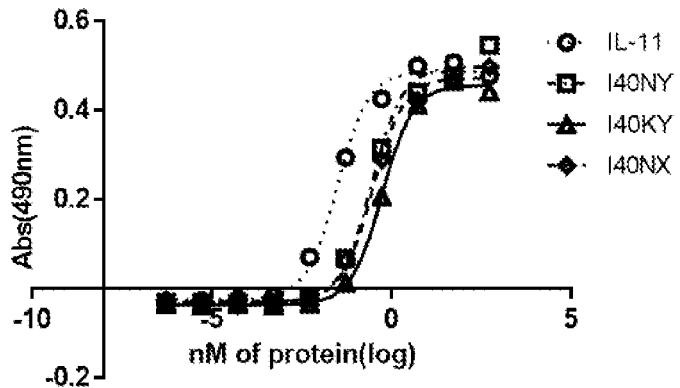

Cell-based Assay for IL-11 Conjugates: The biological activities of conjugated IL-11 were tested in a cell proliferation assay, using 7TD1 cell-line (DSMZ, Germany). In brief, 7TD1 cells at 4,000 cells per well were grown at 37° C. in a humidified atmosphere of 5% $CO_2$ in response to different IL-11 concentrations for two days in the presence of 2 μg/mL murine IL-11 receptor (MyBioSource, USA, MBS553276)(*Biochem. J.*, 318:489-495). After addition of MTS, the EC50 of dose response curve was determined by plotting the absorbance of 490 nm on the y-axis against IL-11 concentrations on the y-axis, by fitting sigmoid dose-response curves with GraphPad software Prism 6. Before animal studies, the biological activities of newly synthesized conjugates were tested in a cell proliferation assay, using 7TD1 cell line. Not all PEGylation preparations gave similar products, and the actual product formation depends on the amino acid residues of the IL-11 being conjugated, and on the size and the shape of the PEG molecule used. 7TD1 cells grew in response to different conjugate concentrations. After addition of developers, whose chemical signal has a linear relationship with the cell number, absorbance at 490 nm was read in an ELISA plate-reader. The results were shown in FIG. 9.

Due to the steric hindrance of the PEG moiety, all the conjugates expectedly showed a reduction in bioactivity in the cell-based assay as compared to that of the un-PEGylated IL-11 with the following order of potency: IL-11 (100%)>I20NL, I20NY (both about 16%)>I40NY, I40NX (both 11%)>I40KY (6%)>I20NY2 (3%). Notably, the steric interference is a dominant factor in determining biological activity of PEGylated conjugates and can be seen as a drastic decrease in bioactivity of the conjugate whose overall PEG moiety is bigger than 20 KDa. From some cell-based studies, there was a report showing that a small carbohydrate attachment at the non-core region of the IL-11 molecule, such as N-terminal sequence, enhanced the biological activity when compared with those conjugates at other attachment sites (*J. Biol. Chem.* Vol 286, No. 10, pp 8085-8093), which was consistent with less reduction of bioactivity by PEG molecule at the N-terminal sequence of IL-11. Although the in vitro bioactivity of I40NY retained only about 11% of native IL-11, in vivo efficacy was beneficially affected and could not be predicted from the in vitro bioactivity data. Table 6 below schematically illustrates bioactivity ratios of various compounds relative to unmodified IL-11.

TABLE 6

| Identification | Bioactivity ratio to unmodified IL-11 |
|---|---|
| IL-11 | 1 |
| I20NL | 0.13 |
| I20NY | 0.16 |
| I20NY2 | 0.03 |
| I40NY | 0.11 |
| I40NX | 0.11 |
| I40KY | 0.06 |

Chemical modification of proteins with PEG is an established technology and has been applied to biopharmaceutical industry to enhance the solubility and physical-chemical stability of proteins. While this chemical reaction is easy to carry out, it often results in a complex mixtures of different PEGylated forms, containing PEGamer and positional isomers. Multiple chromatographic purifications steps are employed to isolate product with high recovery. To develop a commercially viable process in terms of cost and yield, many factors such as protein concentration, quality of PEG, protein/PEG ratio, reaction temperature, and buffer pH, as well as purification process, are required to be optimized.

I40NY was constructed by conjugation with a Y-shaped polyethylene glycol chain on amines forming stable amine bond, with relatively high selectivity to the N-terminal amine driven by conjugation chemistry (reductive amination of aldehyde coupling group in PEG moiety). I40KY on the other hand was conjugated using a functionalized NHS reagent at pH 8 on accessible amines forming the corresponding amide bonds. More specifically, I40NY is the mono-PEGylated IL-11 produced with site-specific reaction under acidic conditions because functionalized aldehyde is largely selective for the N-terminal α-amine, whose pKa is lower compared to other nucleophiles. PEG to protein ratio, reaction concentration, pH and kinetics were investigated in the conjugation reaction. Reactions were taken place for 24 hours at room temperature (22-27° C.) in small scale at about 0.05-0.5 mL in volume in the presence of 10 mM sodium cyanoborohydride. Yield of each reaction under investigation was determined by RP-UPLC. Using different pH for selected reactions, optimum conjugation yield was at pH 4.5-5.5. In addition, the inventors noted that the concentration of reactants played an important factor in product yield and discovered that conjugation with IL-11 at concentrations larger than 5 mg/mL were optimal. Likewise, the PEG to protein ratio and conjugation kinetics of the reaction with 5 mg/mL protein at room temperature in the presence of reducing agent were investigated and suggested an optimum molar ratio of 2 for PEG to protein, and reaction extension to 16 hours sufficient for mono-PEGylation.

Figure 10:
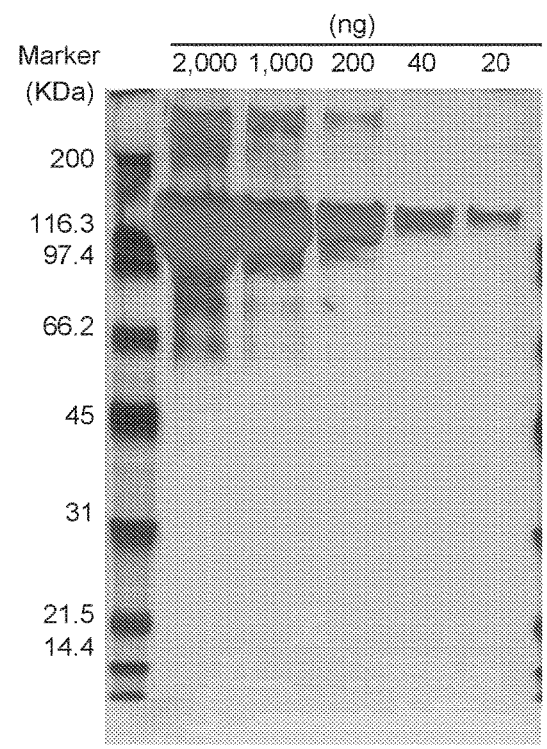
FIG. 10 is an image of a non-reducing SDS-PAGE gel with silver stain illustrating the purity of I40NY at various loading quantities.
Figure 11:
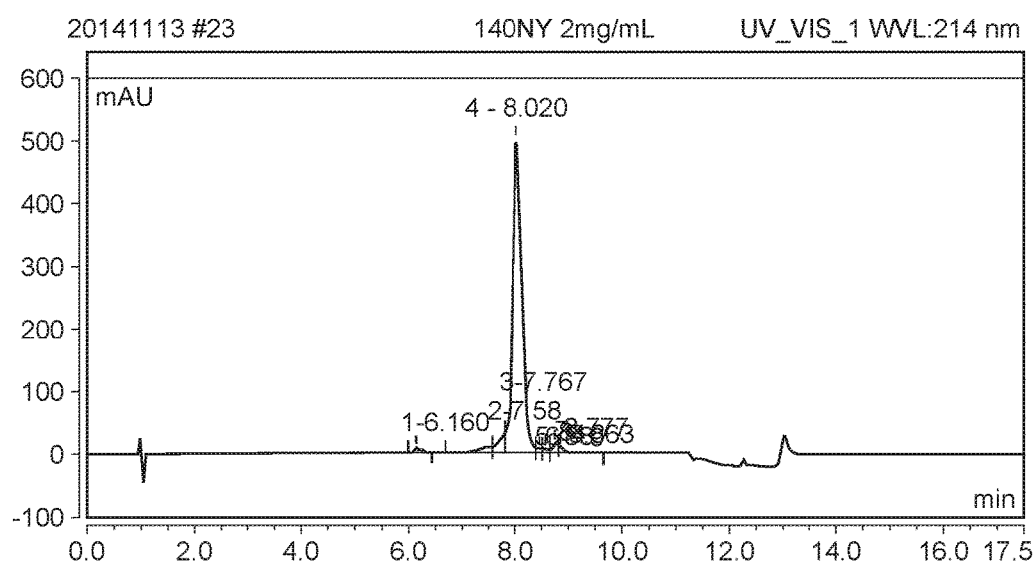
FIG. 11 is a HPLC chromatogram depicting the product purity of mono-PEGylated component for I40NY.

Purification of PEGylated protein usually employs ion-exchange chromatography in large-scale preparation. However a satisfactory resolution to separate the mono-PEGylated from the oligo-PEGylated is not achievable when conventional ion-exchanger is loaded with reaction product at a loading capacity as little as 1 mg/mL resin. The low capacity of this resin often limits its application for larger scale production. To isolate N-terminally mono-PEGylated IL-11 at high purity, various cation-exchange resins were tested. Notably, high porosity resins (e.g., MacroCap SP from GE Healthcare Life Sciences) provided high capacity with retained resolution, and offered high purity and yield of mono-PEGylated targets at high load conditions. The purification process was demonstrated with a batch size of 400 mg IL-11, prepared in 5 mg/mL in sodium phosphate pH 4.5-5 buffer containing 2 molar ratio of aldehyde-activated 40-KD Y-shaped PEG reagent in the presence of 10 mM sodium cyanoborohydride. The reaction solution was quenched by adding 2 M glycine followed by dilution with 4× volume of deionized water. After filtration through a 0.2 μm membrane, the resulting crude was loaded onto a MacroCap SP column (2.6 (diameter)×10 (height) cm at a loading capacity of about 7.5 mg/mL resin). After charging, the column was washed with 20 mM sodium acetate pH 5 buffer over 10 column volume, followed by additional wash with 20 mM sodium acetate pH 5 buffer containing 0.1 M NaCl over 20 column volume. The product was then eluted with 20 mM sodium acetate pH 5 buffer containing 0.3 M NaCl. The overall yield of isolating I40NY was 26.6%. The product purity of I40NY was examined by SDS-PAGE and reverse-phase HPLC, and FIG. 10 shows purity of I40NY on a silver-stained SDS-PAGE gel with quantities of I40NY as indicated above the lanes. The purity of mono-PEGylated IL-11 was larger than 93% as determined by C18-HPLC as the chromatogram displayed in FIG. 11.

Figure 12:
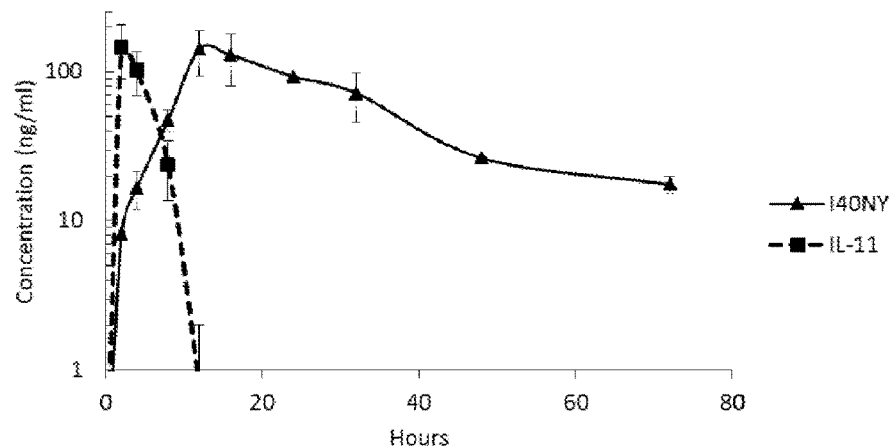
FIG. 12 is a pharmacokinetic profile depicting the kinetics of the plasma concentration of I40NY after single s.c. administration, in comparison to single s.c. administration of unconjugated IL-11.

To determine the pharmacokinetic parameters of I40NY via subcutaneous route, 3 male Sprague-Dawley rats were injected with 0.15 mg/kg of PEGylated IL-11 via single subcutaneous administration. FIG. 12 displayed the plasma concentration of immunoreactive IL-11 in rats after single subcutaneous administration. Plasma concentration of conjugated IL-11 achieved a maximal level at about 12 hr and remained effective over 50 hr after administration. On the contrary, the recombinant human IL-11 reached a maximal concentration at about 2 hr, and was cleared from the circulation blood stream rapidly as the elimination half-life in plasma was about 1.3 hr. The pharmacokinetic parameters of I40NY via subcutaneous route were summarized in Table 7 below.

TABLE 7

| | unit | I40NY | IL-11 |
|---|---|---|---|
| $T_{1/2}$, terminal half-life | hr | 18.6 | 1.1 |
| $T_{max}$, time to maximal concentration | hr | 12 | 2 |
| $C_{max}$, maximal plasma concentration | ng/mL | 142 | 147 |
| $AUC_{all}$, area under curve | Hr*ng/mL | 3947 | 700 |
| $AUC_{inf}$, area under curve to infinity | Hr*ng/mL | 4421 | 701 |
| Vz, relative volume of distribution | mL/kg | 909 | 347 |
| Cl, relative clearance | mL/hr/Kg | 33.9 | 214 |
| MRT, mean residence time | hr | 27.2 | 3.7 |

Figure 13:
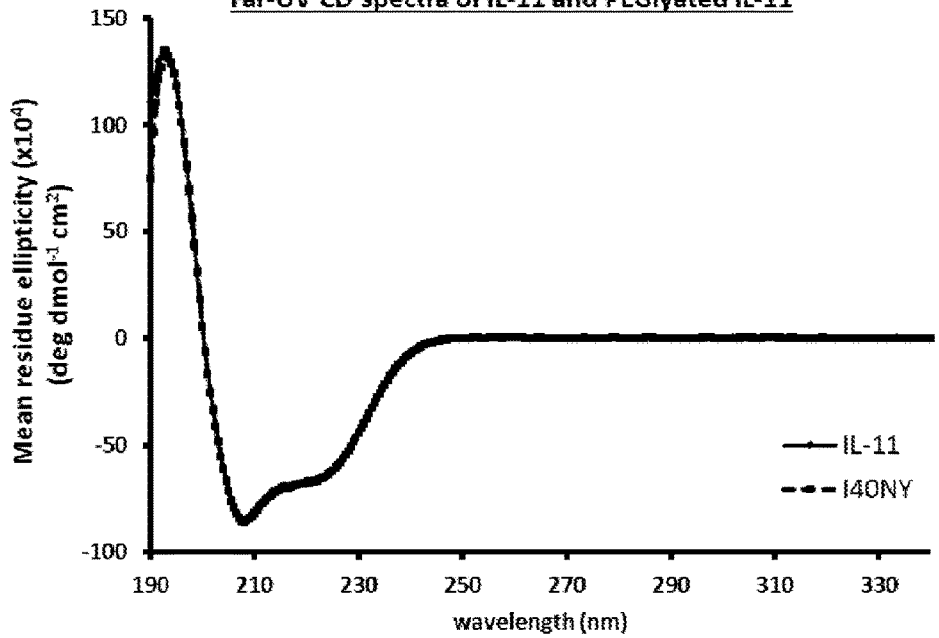
FIG. 13 is an overlay of circular dichroism spectra of IL-11 and I40NY.
Figure 14:
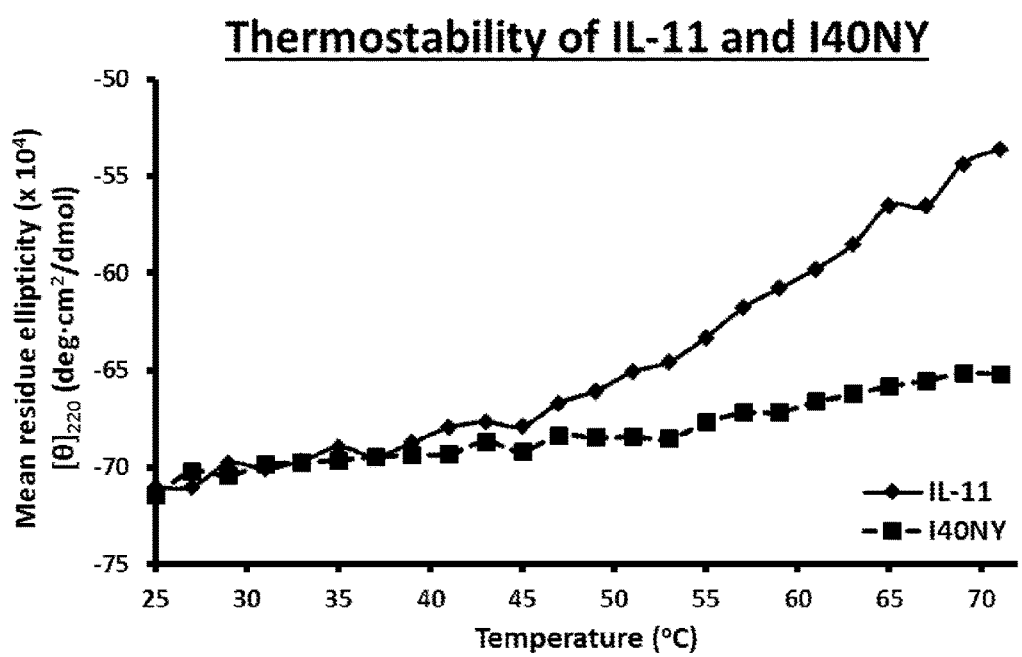
FIG. 14 is an ellipticity plot for IL-11 and I40NY as a function of temperature.

The secondary structure of I40NY was investigated using circular dichroism. In the chromatogram of a circular dichroism analyzed in the far-UV region, the inventors demonstrated that I40NY maintained the same secondary structure as its unconjugated counterpart, as can be seen from both spectra superimposed in FIG. 13. Moreover the thermal stability of I40NY was demonstrated by circular dichroism by measuring the change of their secondary structures (mean residue ellipticity) in response to thermal stress. FIG. 14 indicated the structural change being less for I40NY in response to temperature increment.

Figure 15:
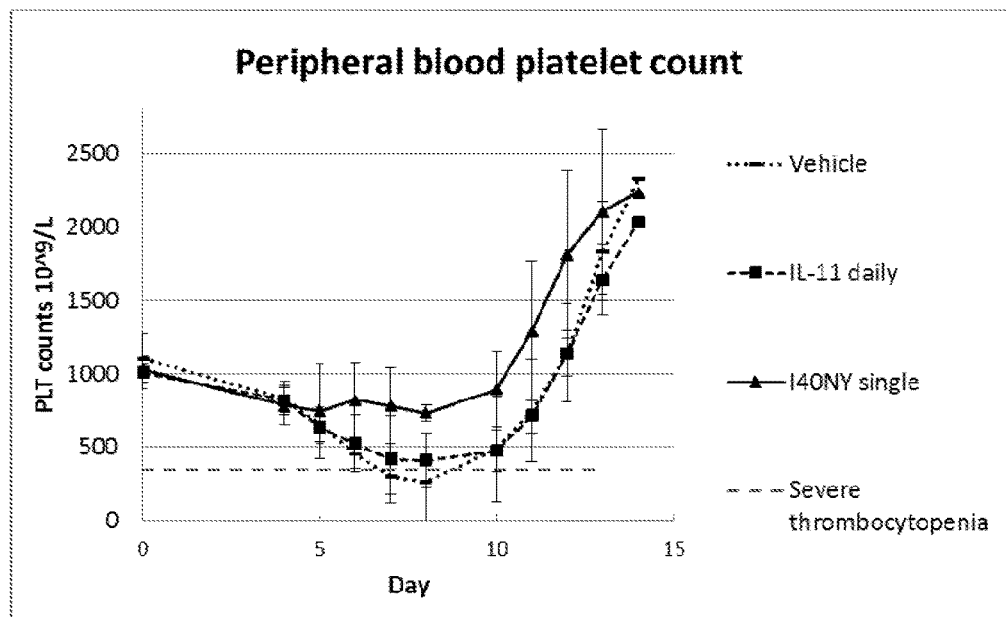
FIG. 15 is a pharmacodynamics profile depicting the platelet production of contemplated compounds in an animal model of myelosuppressive rats.

The effectiveness of I40NY in myelosuppressive rats was also demonstrated in carboplatin-treated rats. Male Sprague-Dawley rats were injected with 40 mg/kg of carboplatin via intravenous administration to induce damaged function of bone marrow leading to thrombocytopenia. Medical intervention using daily injection (consecutive 7 days) of IL-11 or single dose of I40NY at the same 0.15 mg/kg dosage was subcutaneously administered immediately after 24 hours of carboplatin treatment. The platelet level was displayed in FIG. 15. Without treatment, subjects experienced about two days of severe thrombocytopenia (less than ⅓ of normal platelet count), suggesting the untreated having a high risk of life threatening internal bleeding. The efficacy of IL-11 treatment was marginal as the nadir of daily dosing was very close to the threshold of severe thrombocytopenia. Single dose of I40NY, on the contrary, not only prevented the occurrence of severe thrombocytopenia but also accelerated the recovery of platelet levels, as the platelet count returning to the initial number was 1.3 days earlier than the other two groups.

Figure 16:
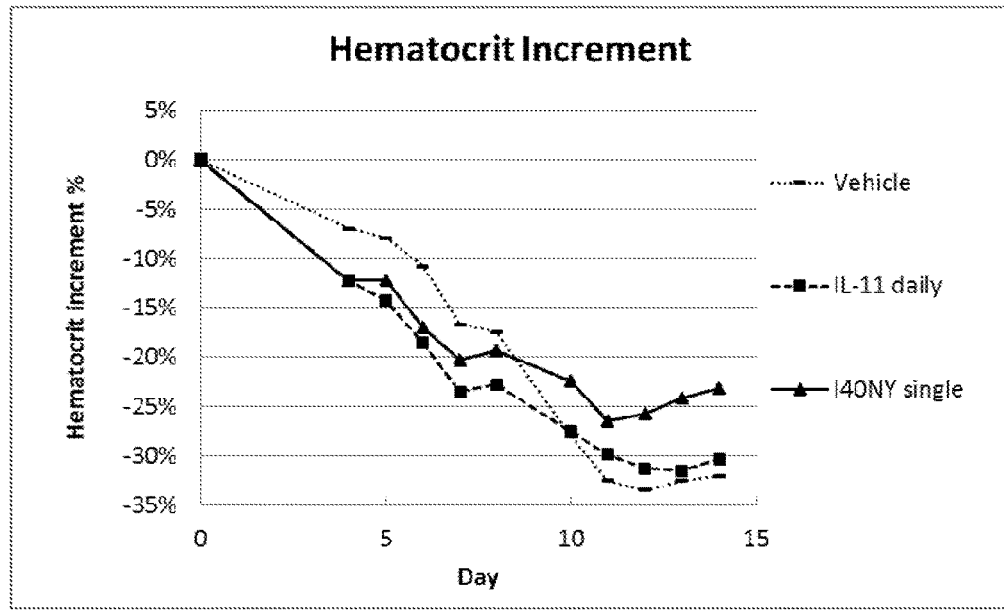
FIG. 16 is a graph depicting the hematocrit reduction of contemplated compounds in an animal model of myelosuppressive rats.

Meanwhile, the side effects as manifested on the reduction of hematocrit was also investigated in the myelosuppressive model. In FIG. 16, treating with IL-11s caused hematocrit reduction in a rapid manner compared to the untreated group. However single dose of I40NY alleviated the nadir, suggesting less intensified side-effect than daily dosing with IL-11. Thus, it should be appreciated that I40NY has proven effective in preventing severe thrombocytopenia induced by chemotherapy, while ameliorating the syndrome of plasma expansion.

Further comparative data between I40NY and another form of a PEGylated IL-11 (as described in U.S. Pat. No. 8,133,480, data not shown) reveal that contemplated compounds, and especially I20NY and I40NY had significantly enhanced in vivo effectiveness and reduced syndrome of side-effect as compared to the other form of PEGylated IL-11 as described in the '480 patent.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

---

---

What is claimed is:

1. A method of increasing serum half-life of an interleukin 11 (IL-11) compound, comprising:
   providing an IL-11 conjugate preparation by covalently coupling an IL-11 polypeptide chain to a PEG moiety by a process that selectively couples the PEG moiety to the N-terminus of the IL-11, wherein the PEG moiety has an average molecular weight of between 10-50 Kd and has at least two branches, and wherein an equimolar to 2-fold molar excess of the PEG moiety relative to the IL-11 is present during coupling;
   wherein the IL-11 conjugate preparation comprises a monosubstituted IL-11 conjugate at a purity of greater than 93%; and
   wherein the IL-11 polypeptide chain is a human IL-11 or truncated human IL-11 polypeptide chain.

2. The method of claim 1 wherein the IL-11 polypeptide chain is a human IL-11 polypeptide chain.

3. The method of claim 1 wherein the IL-11 polypeptide chain is truncated by deletion of an N-terminal proline.

4. The method of claim 1 wherein the IL-11 polypeptide chain has a sequence according to SEQ ID NO:1.

5. The method of claim 1 wherein the PEG moiety has an average molecular weight of 20 Kd or 40 Kd.

6. The method of claim 1 wherein the PEG moiety has a Y shape.

7. The method of claim 1 wherein the PEG moiety is covalently bound to the N terminus via an amine bond.

* * * * *

UNITED STATES PATENT AND TRADEMARK OFFICE
CERTIFICATE OF CORRECTION

PATENT NO. : 10,335,492 B2
APPLICATION NO. : 15/554415
DATED : July 2, 2019
INVENTOR(S) : Kuo-Ming Yu et al.

Page 1 of 1

It is certified that error appears in the above-identified patent and that said Letters Patent is hereby corrected as shown below:

In the Claims

At Column 23, Line 8 Claim 7 change "bound to the N terminus via an amine bond." to --bound to the N-terminus via an amine bond.--

Signed and Sealed this
Fifth Day of January, 2021

Andrei Iancu
*Director of the United States Patent and Trademark Office*